United States Patent
Beilfuss et al.

(10) Patent No.: US 10,640,714 B2
(45) Date of Patent: May 5, 2020

(54) USE OF COMPOSITIONS HAVING A CONTENT OF 3,3'-METHYLENEBIS(5-METHYLOXAZOLIDINE) IN THE REMOVAL OF SULPHUR COMPOUNDS FROM PROCESS STREAMS

(71) Applicant: Schülke & Mayr GmbH, Norderstedt (DE)

(72) Inventors: Wolfgang Beilfuss, Hamburg (DE); Ralf Gradtke, Tornesch (DE); Stefanie Krause, Quickborn (DE); Jennifer Knopf, Hamburg (DE); Michael Streek, Hamburg (DE); Joachim Thiede, Norderstedt (DE); Klaus Weber, Hamburg (DE)

(73) Assignee: VINK CHEMICALS GMBH & CO. KG, Kakenstorf (DE)

( * ) Notice: Subject to any disclaimer, the term of this patent is extended or adjusted under 35 U.S.C. 154(b) by 0 days.

(21) Appl. No.: 16/061,781

(22) PCT Filed: Dec. 13, 2016

(86) PCT No.: PCT/EP2016/080743
§ 371 (c)(1),
(2) Date: Jun. 13, 2018

(87) PCT Pub. No.: WO2017/102693
PCT Pub. Date: Jun. 22, 2017

(65) Prior Publication Data
US 2018/0371334 A1 Dec. 27, 2018

(30) Foreign Application Priority Data
Dec. 14, 2015 (DE) .......... 10 2015 121 689

(51) Int. Cl.
| | | |
|---|---|---|
| C10G 29/20 | (2006.01) |
| C02F 1/68 | (2006.01) |
| C10L 3/10 | (2006.01) |
| C10G 21/27 | (2006.01) |
| B01D 19/00 | (2006.01) |
| B01D 53/74 | (2006.01) |
| B01D 53/78 | (2006.01) |
| C07D 413/06 | (2006.01) |
| C02F 101/10 | (2006.01) |

(52) U.S. Cl.
CPC ......... *C10G 29/20* (2013.01); *B01D 19/0005* (2013.01); *B01D 53/74* (2013.01); *B01D 53/78* (2013.01); *C02F 1/68* (2013.01); *C07D 413/06* (2013.01); *C10G 21/27* (2013.01); *C10L 3/10* (2013.01); *C10L 3/103* (2013.01); *C02F 2101/101* (2013.01); *C10G 2300/202* (2013.01); *C10G 2300/80* (2013.01)

(58) Field of Classification Search
CPC .............. C10G 29/20; C10G 75/00-04; C10G 2300/202; C02F 1/68; C02F 2101/101; B01D 19/0005; B01D 53/74; B01D 53/78
See application file for complete search history.

(56) References Cited

U.S. PATENT DOCUMENTS

| | | | | |
|---|---|---|---|---|
| 5,552,036 A * | 9/1996 | Foret | ............ | C10G 29/20 208/208 R |
| 6,117,310 A * | 9/2000 | Rivers | ............ | C10L 3/10 208/236 |
| 7,078,005 B2 * | 7/2006 | Smith | ............ | C10L 3/10 423/226 |
| 2001/0034366 A1 | 10/2001 | Beilfuss et al. | | |
| 2004/0082473 A1 | 4/2004 | Beilfuss et al. | | |
| 2005/0218379 A1 | 10/2005 | Beilfuss et al. | | |
| 2014/0057817 A1 * | 2/2014 | Janak | ............ | C10G 29/24 507/243 |
| 2014/0209510 A1 * | 7/2014 | Harrington | ............ | C10G 29/20 208/207 |
| 2015/0041411 A1 | 2/2015 | Gradtke et al. | | |

FOREIGN PATENT DOCUMENTS

| | | |
|---|---|---|
| DE | 197 22 858 | 11/1998 |
| DE | 102 44 442 | 4/2004 |
| DE | 10 2004 014 447 | 10/2005 |
| DE | 10 2012 203 003 | 8/2013 |
| WO | WO 98 02501 | 1/1998 |
| WO | WO 02 051968 | 7/2002 |
| WO | WO 2014 004020 | 1/2014 |

OTHER PUBLICATIONS

International Search Report and Written Opinion for corresponding PCT/EP2016/080743, dated Apr. 5, 2017.
Office Action issued in Chinese Patent Application No. 201680079954.3 dated Nov. 5, 2019 with English translation provided.

* cited by examiner

*Primary Examiner* — Renee Robinson
(74) *Attorney, Agent, or Firm* — Young & Thompson

(57) ABSTRACT

The invention relates to the use of a composition comprising a) 3,3'-methylenebis(5-methyl oxazolidine) and b) one or more additives selected from among (i) urea, urea derivatives, amino acids, guanidine and guanidine derivatives and (ii) 1,2-diols in the removal of sulphur compounds from process streams. The composition is preferably used in the removal of hydrogen sulphide from process streams.

20 Claims, No Drawings

USE OF COMPOSITIONS HAVING A CONTENT OF 3,3'-METHYLENEBIS(5-METHYLOXAZOLIDINE) IN THE REMOVAL OF SULPHUR COMPOUNDS FROM PROCESS STREAMS

CROSS REFERENCE TO RELATED APPLICATIONS

This application is a 371 of International Application PCT/EP2016/080743, filed Dec. 13, 2016, which claims priority to German Patent Application 10 2015 121 689.2, filed Dec. 14, 2015, the entire contents of which are incorporated herein by reference.

BACKGROUND

The invention relates to the use of a composition comprising a) 3,3'-methylenebis(5-methyloxazolidine) and b) one or more additives in the removal of sulphur compounds from process streams.

Hydrogen sulphide ($H_2S$) is an unpleasantly smelling, toxic gas which is a great hazard to health and in industrial plants leads to severe corrosion phenomena. Legislators have therefore imposed strict obligations for decreasing the $H_2S$ content. Grotan® OX (3,3'-methylenebis(5-methyl oxazolidine), a water-free condensation product of formaldehyde and isopropanolamine in a molar ratio of 3:2) displays good effectiveness in the chemical neutralization of $H_2S$.

WO 02/051968 A1 discloses a process for decreasing the amount of hydrogen sulphide in a liquid or a gas by treatment with an $H_2S$-scavenging product. The $H_2S$-scavenging product is obtained by reaction of i) a compound having a carbonyl group with ii) an alcohol, thiol, amide, thioamide, urea or thiourea. The product is preferably prepared by reacting formaldehyde with an amine-free alcohol or urea. An example of an amine-free alcohol is ethylene glycol. The $H_2S$-scavenging agent can optionally be used together with amine, in particular monoethanolamine.

WO98/02501 discloses that bisoxazolidines can be used as scavenging agents for sulphhydryl compounds. An example of a bisoxazolidine is 3,3'-methylenebis(5-methyl oxazolidine), which is obtained by reaction of isopropanolamine with formaldehyde (in a molar ratio of 2:3). However, the scavenging action of 3,3'-methylenebis(5-methyl oxazolidine) (hereinafter MBO) for sulphur compounds is in need of improvement, especially in process streams having a low water content. Such process streams are frequently formulated on the basis of hydrocarbons.

According to DE 197 22 858 A1, compositions based on iodopropynylbutylcarbamate and formaldehyde depot compounds are used as preservatives. The addition of particular glycols, preferably 1,2-propylene glycol, has a positive effect on the odour of the compositions and reduces the emission of volatile materials (such as formaldehyde).

DE 102 44 442 A1 discloses a preservative which has a reduced formaldehyde emission and contains a) at least one formal and b) at least one emission-reducing additive selected from among urea, urea derivatives, amino acids, guanidine and guanidine derivatives.

The preservatives described in DE 10 2004 014 447 A1 comprise a) at least N-formal, b) at least one emission-reducing additive and c) monoethylene glycol.

DE 10 2012 203 003 A1 discloses a liquid preparation for reducing free oxygen and preserving water. The preparation comprises a) at least one N-formal and b) at least one dialkylhydroxylamine of the formula RR'NOH (where R and R' are selected independently from among $C_1$-$C_{10}$-alkyl groups).

SUMMARY

It is accordingly an object of the present invention to provide compositions which remove sulphur compounds from process streams, including from process streams which preferably contain little or no water. In particular, $H_2S$-scavenger compositions which have improved efficiency and advantages in use and are additionally also more economical are sought. The compositions should also avoid or reduce precipitates.

These objects are achieved by the use of a composition comprising a) 3,3'-methylenebis(5-methyloxazolidine) and b) one or more additives selected from among (i) urea, urea derivatives, amino acids, guanidine and guanidine derivatives and (ii) 1,2-diols. The composition is, according to the invention, used in the removal of sulphur compounds from process streams.

According to the invention, the composition is preferably used in the removal of hydrogen sulphide from process streams.

It has been found according to the invention that the addition of the additives mentioned improves the effectiveness of compositions containing 3,3'-methylenebis(5-methyl oxazolidine) in the removal of sulphur compounds from process steams compared to the use of 3,3'-methylenebis(5-methyl oxazolidine) alone (i.e. without the additives mentioned). Examples of sulphur compounds which are, according to the invention, removed from the process stream or whose content in the process stream is decreased, are $H_2S$, mercaptans, mercaptides, inorganic and organic sulphides and other thiol compounds.

DESCRIPTION OF PREFERRED EMBODIMENTS

In a first aspect, the invention thus provides for the use of a composition comprising:
a) 3,3'-methylenebis(5-methyl oxazolidine) and
b) one or more additives selected from among:
(i) urea, urea derivatives, amino acids, guanidine and guanidine derivatives and
(ii) 1,2-diols,
in the removal of sulphur compounds from process streams.

The composition used according to the invention is preferably in the form of a concentrate and comprises from 60 to 99% by weight of 3,3'-methylenebis(5-methyl oxazolidine), preferably from 70 to 97% by weight, in particular from 80 to 92% by weight.

In a first preferred embodiment, the composition comprises:
b) one or more additives selected from among urea, urea derivatives, amino acids, guanidine and guanidine derivatives. Examples of such additives are glycoluril, tetramethylolglycoluril, dimethylhydantoin, dimethyloldimethylhydantoin, dimethylolurea, tetramethylolurea, imidazolidinylurea and diazolidinylurea.

The composition particularly preferably comprises b) urea. Here, preference is given to the composition being in the form of a concentrate and comprising b) from 1 to 20% by weight of urea, preferably from 2 to 14% by weight, in particular from 2.5 to 8% by weight, for example from 3 to 6% by weight, of urea.

In a second preferred embodiment, a composition comprising b) one or more 1,2-diols is used. In this embodiment, preference is given to the composition being in the form of a concentrate and comprising b) from 1 to 25% by weight of 1,2-diol, preferably from 3 to 20% by weight, in particular from 5 to 15% by weight, of 1,2-diol. Preferred 1,2-diols used according to the invention are selected from among ethylene glycol, propyleneglycol and mixtures thereof, with component b) preferably being ethylene glycol.

In a third preferred embodiment, the composition used according to the invention comprises b) at least one component (i) and at least one component (ii). In this embodiment, preference is again given to the composition being in the form of a concentrate and comprising b) (i) from 1 to 20% by weight of urea, preferably from 2 to 14% by weight, in particular from 2.5 to 8% by weight, for example from 3 to 6% by weight of urea. It is further preferred in this embodiment that the composition comprises b) (ii) from 1 to 25% by weight of 1,2-diol, preferably from 3 to 20% by weight, in articular from 5 to 15% by weight, of 1,2-diol.

Particular preference is thus given according to the invention to using compositions comprising:
a) from 60 to 99% by weight of 3,3'-methylenebis(5-methyloxazolidine), (preferably from 70 to 97% by weight, in particular from 80 to 92% by weight, of 3,3'-methylenebis (5-methyl oxazolidine)),
b) (i) from 1 to 20% by weight of urea (preferably from 2 to 14% by weight, in particular from 2.5 to 8% by weight, for example from 3 to 6% by weight, of urea) and
b) (ii) from 1 to 25% by weight of 1,2-diol (preferably from 3 to 20% by weight, in particular from 5 to 15% by weight, of 1,2-diol).

Apart from the compulsory components a) 3,3'-methylenebis(5-methyl oxazolidine) and b) one or more of the additives mentioned, the composition can further comprise c) N,N-dialkyl hydroxylamine of the formula RR'NOH, where R and R' are selected independently from among linear, branched and cyclic $C_1$-$C_{10}$-alkyl groups. A preferred N,N-dialkyl hydroxylamine is N, N-diethyl hydroxylamine.

Process streams treated according to the invention are, for example, liquid and gaseous process streams.

Exemplary process streams contain no more than 40% by weight of water, preferably not more than 35% by weight of water, particularly preferably not more than 30% by weight of water, for example not more than 25% by weight or not more than 20% by weight or not more than 15% by weight, for example not more than 10% by weight or not more than 5% by weight, for example not more than 1% by weight, of water.

Fields of use are, inter alia, biogas plants, petroleum and natural gas extraction, processing, storage and transport of fossil energy carriers and the removal of $H_2S$ liberated by sulphate-reducing bacteria under anaerobic conditions. Examples of $H_2S$-containing streams or products are petroleum, crude oil, mineral oil, heating oil, diesel fuel, bitumen, distillation residues, drilling fluids and wastewater. Particular preference is given to the use according to the invention of the compositions in process streams which are hydrocarbon streams.

In a second embodiment, the invention relates to a process for removing one or more sulphur compounds from a process stream, wherein the process stream containing the sulphur compound or sulphur compounds is brought into contact with a composition comprising a) 3,3'-methylenebis (5-methyl oxazolidine) and b) one or more additives selected from among (i) urea, urea derivatives, amino acids, guanidine and guanidine derivatives and (ii) 1,2-diols.

The use is preferably at elevated temperature (for example 50° C. or above, e.g. 70° C. or above, 90° C. or even 150° C. or above). Subsequent liberation of $H_2S$ advantageously does not occur to the same extent as in the case of the sole use of 3,3'-methylenebis(5-methyl oxazolidine). The compositions used according to the invention are better suited for binding the inherent $H_2S$ which is gradually formed subsequently during prolonged hot storage than is 3,3'-methylenebis(5-methyl oxazolidine) alone.

The constituents according to the invention can be introduced individually into the $H_2S$-containing process streams, either within a short time interval or at different points in time. Surprisingly, there is reduced formation of troublesome insoluble deposits or precipitates, sometimes such precipitates are even dissolved. Compositions used according to the invention also have a very good short-term and in particular long-term action. Rapid and efficient lowering of the $H_2S$ content is achieved at short contact times.

The advantages of the invention can be seen, in particular, from the following examples. Percentages are by weight, unless indicated otherwise.

Examples

Composition OX (Comparison):

The reaction product of isopropanolamine and paraformaldehyde (91% strength) in a molar ratio of 2:3 is formed. 3,3'-Methylenebis(5-methyl oxazolidine) is formed here. The water of reaction and the water from the paraformaldehyde are distilled off.

Composition OK (According to the Invention):

The reaction product of isopropanolamine and paraformaldehyde (91% strength) in a molar ratio of 2:3 is formed. 3,3'-Methylenebis(5-methyl oxazolidine) is formed here. The water of reaction and the water from the paraformaldehyde are distilled off. Urea and ethylene glycol are added (the mixture contains about 4.6% by weight of urea and about 9.5% by weight of ethylene glycol).

Method of determining the sulphide concentration (based on IP 570, Determination of hydrogen sulphide in mineral oils)

Contacting of the various sulphur-scavenging agents with the sample at various temperatures and for different times Dilution of the sample with alkylbenzene in order to bring it into the linear working range of the analytical system Injection of the test sample (including sulphur-scavenging agent) into the analytical system Addition of acid (2M $H_3PO_4$ in water) and optionally heating of the analytical sample in the analytical system Quantitative driving-off of the resulting hydrogen sulphide in the analytical system by means of air and transfer of the hydrogen sulphide to an electrochemical measuring electrode in the analytical instrument The hydrogen sulphide produces a measurement signal which is proportional to the respective amount of hydrogen sulphide at the electrochemical measuring electrode.

The peak area formed (made up of measurement signal intensity versus time) is determined by means of evaluation software and converted into a sulphide content on the basis of a calibration line.

a) H₂S in $C_{10-13}$-alkylbenzene (sulphide concentration 200 ppm), 20° C., 2 h

|  | Lowering of the sulphide content % |
|---|---|
| 1000 ppm OX (comparison) | 8.8 |
| 1000 ppm OK (invention) | 11.6 | b) H₂S in $C_{10-13}$-alkylbenzene (sulphide concentration 100 ppm), 50° C.

|  | Lowering of the sulphide content % | | |
|---|---|---|---|
|  | 1 h | 2 h | 3 h |
| 1000 ppm OX (comparison) | 6.7 | 6.2 | 3.8 |
| 1000 ppm OK (invention) | 9.6 | 10.2 | 11.4 | c) H₂S in $C_{10-13}$-alkylbenzene (sulphide concentration 200 ppm), 50° C., 2 h

|  | Lowering of the sulphide content % |
|---|---|
| 1000 ppm OX (comparison) | 10.0 |
| 1000 ppm OK (invention) | 15.4 |

These examples demonstrate that compositions used according to the invention not only decrease the sulphide content better than does 3,3'-methylenebis(5-methyloxazolidine) alone, but that this improved effect is even more pronounced at an elevated use temperature.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A method for removing sulphur compounds from liquid or gaseous process streams comprising a step of contacting the liquid or gaseous process stream with a composition comprising:
   a) 3,3'-methylenebis(5-methyloxazolidine) and
   b) urea.

2. The method according to claim 1, characterized in that the composition is in the form of a concentrate and comprises from 60 to 99% by weight of 3,3'-methylenebis(5-methyloxazolidine).

3. The method according to claim 2, characterized in that the composition is in the form of a concentrate and comprises from 70 to 97% by weight of 3,3'-methylenebis(5-methyloxazolidine).

4. The method according to claim 3, characterized in that the composition is in the form of a concentrate and comprises from 80 to 92% by weight of 3,3'-methylenebis(5-methyloxazolidine).

5. The method according to claim 1, characterized in that the composition is in the form of a concentrate and comprises from 1 to 20% by weight of urea.

6. The method according to claim 5, characterized in that the composition is in the form of a concentrate and comprises from 2 to 14% by weight of urea.

7. The method according to claim 6, characterized in that the composition is in the form of a concentrate and comprises from 2.5 to 8% by weight of urea.

8. The method according to claim 1, characterized in that the composition further comprises one or more 1,2-diols.

9. The method according to claim 8, characterized in that the composition is in the form of a concentrate and comprises from 1 to 25% by weight of 1,2-diol.

10. The method according to claim 9, characterized in that the composition is in the form of a concentrate and comprises from 3 to 20% by weight of 1,2-diol.

11. The method according to claim 10, characterized in that the composition is in the form of a concentrate and comprises from 5 to 15% by weight of 1,2-diol.

12. The method according to claim 8, characterized in that the 1,2-diol is selected from the group consisting of ethylene glycol, propylene glycol and mixtures thereof.

13. The method according to claim 12, characterized in that the 1,2-diol is ethylene glycol.

14. The method according to claim 1, characterized in that the composition further comprises c) N,N-dialkyl hydroxylamine of the formula RR'NOH, where R and R' are selected independently from among linear, branched and cyclic $C_1$-$C_{10}$-alkyl groups.

15. The method according to claim 14, characterized in that the N,N-dialkyl hydroxylamine is N,N-diethyl hydroxylamine.

16. The method according to claim 1, characterized in that the process stream contains not more than 40% by weight of water.

17. The method according to claim 1, characterized in that the process stream is a hydrocarbon stream.

18. The method according to claim 1, characterized in that the sulphur compound is selected from the group consisting of hydrogen sulphide, inorganic and organic sulphides, mercaptans and mercaptides.

19. The method according to claim 18, characterized in that the sulphur compound is hydrogen sulphide.

20. A method for removing sulphur compounds from process streams comprising a step of contacting the process stream with a composition comprising:
   a) 3,3'-methylenebis(5-methyloxazolidine) and
   b) urea,
   wherein the process streams are selected from the group consisting of hydrocarbon streams, petroleum, crude oil, mineral oil, heating oil, diesel fuel, bitumen, distillation residues, drilling fluids and wastewater.

* * * * *